United States Patent
Jaeger

(10) Patent No.: US 6,807,873 B2
(45) Date of Patent: Oct. 26, 2004

(54) DRY MATERIAL SAMPLER AND METHOD

(76) Inventor: Ben E. Jaeger, 50 Hunter La., Bristol, IL (US) 60512

( * ) Notice: Subject to any disclaimer, the term of this patent is extended or adjusted under 35 U.S.C. 154(b) by 198 days.

(21) Appl. No.: 10/084,966

(22) Filed: Feb. 27, 2002

(65) Prior Publication Data

US 2003/0159524 A1 Aug. 28, 2003

(51) Int. Cl.$^7$ ................................................. G01N 1/00
(52) U.S. Cl. .................................................. 73/863.83
(58) Field of Search ........................ 73/863.51, 863.52, 73/863.83–863.85, 863.34

(56) References Cited

U.S. PATENT DOCUMENTS

| | | | |
|---|---|---|---|
| 3,949,614 A | * 4/1976 | Abonnenc | ................ 73/863.83 |
| 4,147,062 A | 4/1979 | Jaeger | |
| 4,262,533 A | 4/1981 | Jaeger | |
| 4,475,410 A | 10/1984 | Jaeger | |
| 4,630,479 A | * 12/1986 | Wagener et al. | ......... 73/863.83 |
| 4,744,255 A | 5/1988 | Jaeger | |
| 6,164,145 A | 12/2000 | Jaeger | |

* cited by examiner

Primary Examiner—Robert Raevis
(74) Attorney, Agent, or Firm—Pyle & Piontek

(57) ABSTRACT

A sampling apparatus is characterized by a sampler for obtaining samples of a dry product from a vessel. The sampler has a bore with a forward opening in communication with the product in the vessel. A plunger of the sampler has an annular recess intermediate its ends, and is manually extended forward in the bore to project the recess through the bore forward opening and into the vessel to receive a product sample in the recess. The plunger is then manually retracted rearward from the vessel to convey the product sample in its recess to a sample collection point in the sampler bore. When the plunger recess is at the sample collection point, a length of open bore exists between the front of the plunger and the bore forward opening. So that product from the vessel does not enter the bore opening and accumulate in and block the bore in front of the plunger, after collection of the sample, the plunger is manually extended forward to a parked position. When in the parked position, the front of the plunger is close to and preferably at the bore forward opening to close the bore to entry of product from the vessel. The plunger is then locked in the parked position until another product sample is to be obtained.

27 Claims, 3 Drawing Sheets

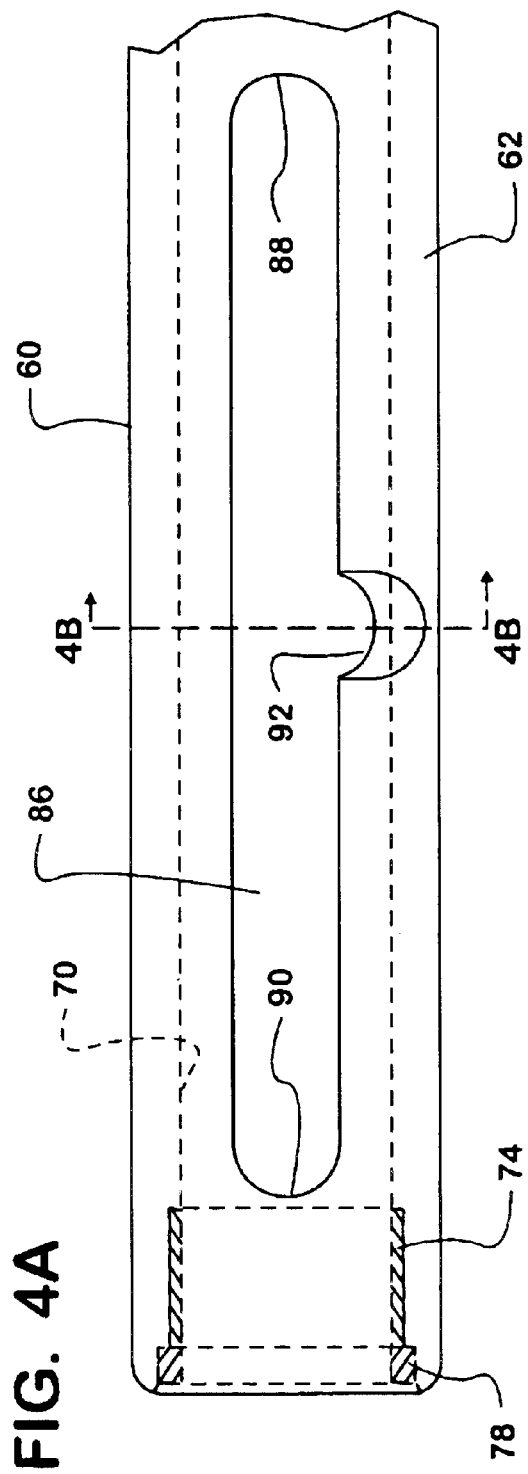
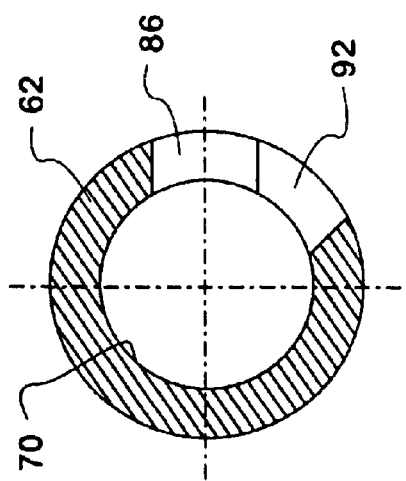
FIG. 4A
FIG. 4B

DRY MATERIAL SAMPLER AND METHOD

BACKGROUND OF THE INVENTION

The present invention relates to methods of and apparatus for extracting samples of a dry material product from a main body of product in a tank or vessel.

Various manufacturing operations require that the immediate or overall composition of a product be monitored. Such monitoring may be accomplished with samplers for taking samples of the product from a main body of the product. When a composite sample is required, the sampler may be periodically operated to withdraw small samples of product from the main body, which samples are mixed together and represent a composite of the main body of product. Other uses for samplers are in applications in which the immediate composition of a product must be determined. In this case, the samples are individually analyzed.

To obtain samples of a dry material product, some samplers divert material from the main body of product and from the diverted material samples are removed in various ways. Attempts to withdraw small samples of a dry product directly from a main body of product, however, have presented many problems not altogether satisfactorily solved. For example, where product receiving holes or slots in a sampler are extended directly into a vessel, sampled product can build up in such holes and slots and either block the same or contaminate subsequent samples.

Other samplers utilize a plunger that is extended through a sampler body bore into a main body of product to receive a sample of product in a sample-receiving opening in the plunger. The plunger is then retracted to convey the sample to a collection point. Four samplers of this type are disclosed in U.S. Pat. Nos. 4,147,062, 4,262,533, 4,475,410 and 4,744,255, issued to the present inventor and the teachings of all of which are incorporated herein by reference. These samplers are primarily adapted to sample liquid products, and are attached to an access line to a vessel containing liquid product to be sampled, so that a sample-receiving opening in a plunger of the sampler can be extended into the product in the vessel to obtain a sample of product. The plunger is then retracted to deliver the sample to a collection point.

When a plunger-type sampler is idle, its plunger normally is refracted and the front of the plunger is rearward from a forward opening from the sampler bore. The forward end of the bore, between the front of the plunger and the opening, is then exposed to and can fill with product from the vessel. If the sampler is idle sufficiently long, product from the vessel may fill, coalesce in and block the sampler bore in front of the plunger. The blockage can then disable the sampler by preventing subsequent reciprocation of the plunger to obtain samples.

U.S. Pat. No. 6,164,145, issued to the present inventor and the teachings of which are incorporated herein by reference, addresses the problem of product collecting in and clogging a forward end of a sampler bore in front of a plunger when the sampler is idle. According to this patent, when a sampler is to be idle, the sampling plunger is moved to a parked position in the sampler bore, where the forward end of the plunger is very close to or at the forward opening from the bore. The plunger then serves to close the opening to the bore, so that product in the vessel cannot enter and collect in the bore in front of the plunger. This technique prevents potential contamination of subsequent samples and ensures that the sampler is not rendered inoperative by product clogging the front of the bore.

The sampler of said U.S. Pat. No. 6,164,145 is advantageous for use with liquid products that tend collect in and to block a sampler bore, such as a product comprising paper pulp, but it is not well adapted for sampling a dry material product. Such a dry product could comprise, for example, a dry food product comprising various dry ingredients that are separately introduced into and mixed in a blender. In the case of such a product, it often is desirable at to obtain samples of the product various stages of mixing to determine the extent to which the individual ingredients have been mixed together and when the product has been fully and properly blended. The prior art does not provide a plunger-type sampler that is suitable for sampling such a dry material product.

OBJECTS OF THE INVENTION

An object of the present invention is to provide a sampler that is adapted to sample a dry material product.

Another object of the present invention is to provide such a sampler of the reciprocating plunger type.

A further object is to provide such a sampler that, when idle, cannot be disabled by product entering and blocking a sampler bore within which the plunger is reciprocated.

Yet another object is to provide such a sampler in which the length of the sampler bore forward from the plunger is minimized when the sampler is idle.

A still further object is to provide such a sampler in which the plunger is at a first position in the sampler bore when delivering a product sample at a sample collection point in the bore, is at a second position in the bore when the sampler is idle, and is at a third position in the bore when obtaining a product sample.

SUMMARY OF THE INVENTION

In accordance with the present invention, a sampling apparatus comprises a sampler that is operable to obtain discrete samples of a dry material product from a main body of product. The sampler includes a sampler body having a bore with a forward opening, and plunger means having a product sample receiving opening is in the bore. Means are provided to reciprocate the plunger means in the bore to a sample receiving position where the plunger means sample receiving opening is extended forward out of the forward bore opening, to a sample delivering position where the plunger means sample receiving opening is retracted rearward to a sample collecting point in the bore, and to a parked position in the bore intermediate the sample receiving and delivering positions where the plunger means closes the forward opening from the bore. In addition, included is means for locking and unlocking the plunger means against and for reciprocation when the plunger means is in the parked position.

In the described embodiment of sampling apparatus, the plunger means has a forward end that is positioned rearward from the forward opening from the bore when the plunger means is in the sample delivering position, and that is positioned close to and preferably at the forward opening when the plunger means is in the parked position. The plunger means sample receiving opening comprises an annular recess in and circumferentially around the plunger means, and the plunger means and the means for reciprocating are connected for conjoint reciprocation. The means for locking and unlocking the plunger means locks and unlocks the means for reciprocating against and for reciprocation when the plunger means is in the parked position.

The means for reciprocating the plunger means is manually actuated and includes a handle for being moved by an operator and a driver rod connected at one end to the handle and at an opposite end to the plunger means. Means are provided for guiding and controlling the extent of reciprocation of the handle, driver rod and plunger means, which means includes a guide sleeve around the driver rod, a longitudinal slot in the guide sleeve and a stop carried by the driver rod and extending into the slot. The stop reciprocates in the slot with reciprocation of the driver rod in the guide sleeve, so that the slot guides the stop, handle, driver rod and plunger means during reciprocation. The slot has forward and rearward ends that are engaged by the stop to limit the extent of forward and rearward reciprocation of the plunger means.

The means for locking and unlocking the plunger means against and for reciprocation includes means for locking and unlocking the stop against and for reciprocation in the guide sleeve slot when the plunger means is in the parked position. Such means for locking and unlocking includes a circumferential extension of the slot that extends generally perpendicular to the longitudinal extent of the slot. The stop is moved into the circumferential slot extension when the plunger means is in the parked position to lock the stop and thereby the plunger means against reciprocation, and the stop is moved out of the circumferential slot extension to unlock the plunger means for reciprocation. The handle, drive rod, stop and plunger means are conjointly rotated when the plunger means is in the parked position to move the stop into and out of the circumferential extension.

The invention also contemplates a method of obtaining samples of a dry material product, which comprises the steps of providing a sampler body having a longitudinal bore and a forward opening from the bore, and positioning in the bore a plunger having a sample receiving recess intermediate forward and rearward ends of the plunger. Included are the steps of extending the plunger forward through the bore to a plunger sample receiving position where the forward end and recess of the plunger are projected out of the bore opening into a body of dry product to receive in the recess a sample of product, then retracting the plunger rearward through the bore opening to a plunger sample delivering position to convey the product sample in the recess to a sample collecting point, and then removing the sample from the plunger recess at the sample collecting point. When the plunger is at the sample delivering position, its forward end is spaced rearward from the bore opening, so that a length of open bore then exists between the plunger forward end and the opening from the bore, into which product from the body of product can enter and accumulate. To prevent product from entering and stagnating in the length of open bore and potentially clogging the bore, after performance of the step of removing the product sample from the plunger recess, included is the step of moving the plunger forward to a parked position, intermediate the sample delivering and receiving positions, where the forward end of the plunger closes the opening to the bore. The step is then performed of locking the plunger in the parked position.

The step of moving the plunger to the parked position comprises moving the plunger to position its forward end close to and preferably at the bore opening, so that the plunger forward end then closes the bore and prevents entry into the bore of dry product from the body of dry product Each of the plunger extending, retracting and moving steps is manually performed.

The foregoing and other objects, advantages and features of the invention will become apparent upon a consideration of the following detailed description, when taken in conjunction with the accompanying drawings.

BRIEF DESCRIPTION OF THE DRAWINGS

FIG. 4A is a fragmentary top plan view of a guide of the sampler, showing a slot in the guide for receiving and guiding a stop that controls reciprocation of the plunger, and FIG. 4B is a cross-sectional side elevation view taken substantially along the lines 4B—4B of FIG. 4A, showing an extension of the slot that accommodates locking the plunger against reciprocation.

DETAILED DESCRIPTION

The invention comprises a product sampling apparatus having a sampling plunger that is manually reciprocated in a sampler body bore between the extremes of sample receiving and sample delivering positions. The sampling apparatus is adapted to be attached to a vessel containing a main body of a dry material product to be sampled. To obtain a product sample the plunger is extended forward through an open forward end of the sampler body bore to the sample receiving position to place a sample receiving opening in the plunger in the product in the vessel to receive a product sample in the opening. The plunger is then retracted from the vessel into the bore to the sample delivering position to convey the product sample to a sample collecting point. When the plunger is in the sample delivering position, the front of the plunger is sufficiently rearward from the bore forward opening that, if the sampling apparatus remains idle, product from the vessel can enter and block the bore in front of the plunger and disable the sampling apparatus by preventing further reciprocation of the plunger. To avoid any such blockage of the bore, the invention contemplates that the plunger be manually moved to and locked in an intermediate parked position when the sampler is idle, in which parked position the front of the plunger is closely adjacent to and preferably at the forward opening from the bore. The plunger then closes the bore to entry of product that could otherwise accumulate in and block the bore in front of the plunger.

In a contemplated use of the sampling apparatus, there is no pressure of the product in the vessel and the product may be a dry food product that can have a consistency ranging from a flour-like material to more coarse materials such as Grape Nut® cereal and Shake-N'-Bake® breading. In the preparation of such food products, the various individual ingredients making up the product are put into a mixer for being blended together into the final product, and the sampling apparatus can be used at various stages of the mixing and blending process to determine the extent of mixing that has occurred and when the composite product is properly and fully blended. It is understood that while a contemplated use of the sampling apparatus is in the preparation of food products, the apparatus is suitable for use with other than food products.

Figure 1:
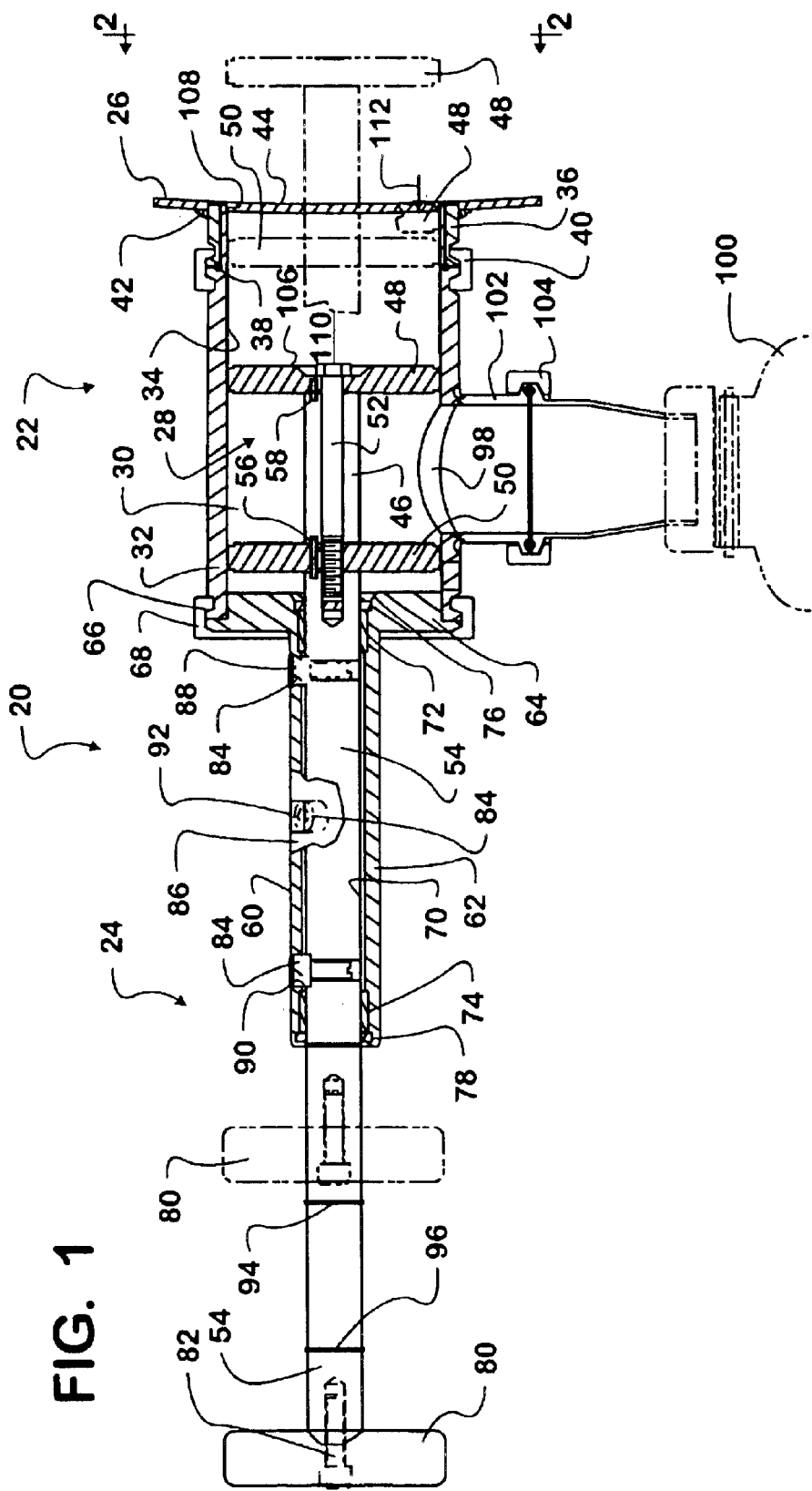
FIG. 1 is a cross-sectional side elevation view of a plunger-type sampler embodying the teachings of the present invention, showing a plunger of the sampler in each of sample receiving, sample delivering and parked positions.
Figure 2:
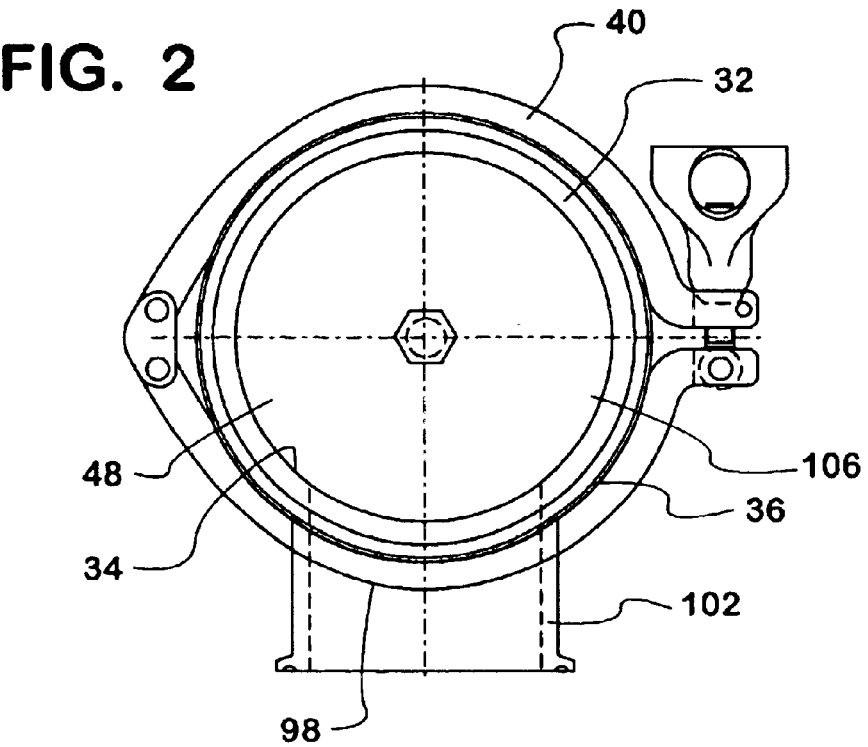
FIG. 2 is a view taken substantially along the lines 2—2 of FIG. 1, except that a product containing vessel in FIG. 1 is not shown.

Referring to FIG. 1, the sampling apparatus is indicated generally at 20 and includes a sampler and a motor means for operating the sampler, respectively indicated at 22 and 24. The sampling apparatus may be used to obtain samples of a dry material product from a main body of dry product contained a vessel 26, and includes a plunger assembly, indicated generally at 28, having a sample receiving opening, such as an annular recess 30. The plunger is extended into the vessel to a plunger sample receiving position to receive in the recess a sample of dry product from the main body of product in the vessel. The plunger is then retracted from the vessel to a plunger sample delivering position to convey the product sample in the recess to a sample collection point in the sampler 22. The recess can be sized to receive and contain a selected volume of product and individual product samples delivered to the collection point can be separately analyzed. Alternatively, if the sampling operation so requires, a number of product samples can be delivered to the collection point and mixed together before analysis. The motor means 24 for reciprocating the plunger assembly can be manually operated, as shown, or it can be any other suitable type of motor means, such as pneumatic or electric motor means.

The sampler 22 has a body 32 with a longitudinal bore 34 in which the plunger assembly 28 reciprocates. A forward end of the sampler body is circumferentially stepped and received in a rearward end of a passage through an adapter 36. An O-ring seal 38 seals the sampler body to the adapter and a quick connect/disconnect clamp 40 attaches the sampler body to the adapter. A forward end of the adapter is welded at 42 to the vessel around an opening 44 to the vessel that provides communication for the sampler with the interior of the vessel and dry product therein.

The plunger assembly 28 is spool-shaped and comprises a cylindrical spacer 46, a circular cap 48 at a forward end of the spacer and a circular carrier 50 at a rearward end of the spacer. The spacer, cap and carrier are held together and attached to the motor means 24 by a bolt 52 that extends axially through the spacer, cap and carrier into threaded attachment to a forward end of a cylindrical driver rod 54 of the motor means. A pin 56 extends through the carrier 50 and into and between the driver 54 and spacer 46, and a pin 58 extends into and between the spacer and cap 48. The pins 56 and 58 prevent relative rotation between the driver, carrier, spacer and cap to ensure that in operation of the sampling assembly 20, the bolt 52 remains tightly threaded into the forward end of the driver rod 54 and the plunger assembly does not become loose.

The motor means 24 for reciprocating the sampler plunger assembly 28 includes the driver 54 and a guide 60 around the driver. The guide comprises an elongate rearward tubular part 62 and an increased diameter annular forward part 64 that has a stepped circumferential recess 66 in which a rearward end of the sampler body 32 is received. The motor means 24 and sampler 22 are connected by a quick connect/disconnect clamp 68, with the forward part 64 of the guide 60 then closing the rearward end of the sampler body bore 34. The driver 54 extends through a bore 70 in the guide 60 and is supported for reciprocation in the bore by forward and rearward bushings 72 and 74. Forward and rearward filled Teflon® wipers 76 and 78 are at opposite ends of the bore and a handle 80 for being pushed, pulled and rotated by an operator is attached to a rearward end of the driver by a fastener 82 to accommodate manual reciprocation of the driver and plunger assembly 28 and locking of the plunger assembly in the parked position. For strength and to facilitate reciprocation of the plunger assembly through the sampler body bore 34, the plunger assembly cap 48 and carrier 50 are made of Teflon® coated stainless steel.

Means are provided to guide and limit the extent of forward and rearward reciprocation of the plunger assembly 28 and to lock the plunger assembly in its parked position. Such means includes a stop 84 carried by the motor means driver rod 54 and extending outward from the driver. The stop is received in a slot 86 extending through and longitudinally along the guide tubular part 62. The slot has forward and rearward ends 88 and 90 that the stop abuts to limit the maximum extent of forward and rearward reciprocation of the driver and plunger assembly. The slot also has an intermediate circumferential extension 92 into which the stop can be moved when the plunger assembly is in its parked position in order to prevent reciprocation of the plunger assembly and lock the plunger assembly in the parked position. Indicators 94 and 96 on the driver 54, which may take the form of circumferential grooves, provide an operator with a visual indication of the position of the plunger assembly.

Figure 3:
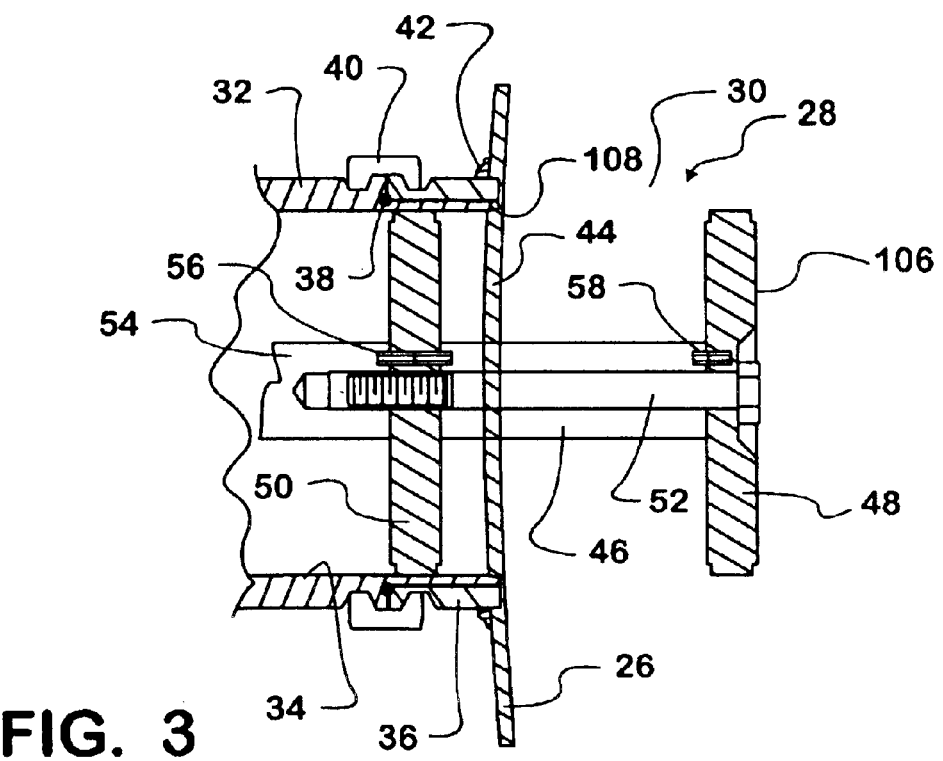
FIG. 3 is a fragmentary cross-sectional side elevation view of the forward end of the sampler, showing the plunger in the sample receiving position.

In operation of the sampler assembly 20, and beginning with the sampler assembly in the condition shown in solid line in FIG. 1, a product sample is collected from the vessel 26 by manually moving the handle 80 rightward and forward. This reciprocates the driver 54 and plunger assembly 28 forward to extend the plunger assembly cap 48 and annular sample receiving opening 30 through the sampler body bore 34 and into the main body of dry product in the vessel interior. The handle and plunger assembly are moved rightward until further movement is blocked by engagement of the stop 84 with the forward end 88 of the slot 86 in the guide 60, at which point the plunger assembly is fully in its sample receiving position, as shown in phantom line in FIG. 1 and solid line in FIG. 3. Also at this point, the indicator line 96 on the driver is moved to adjacent the rearward end of the guide 60 to visually inform the operator that the plunger assembly has moved fully to its sample receiving position and that further forward movement is not being prevented because of any obstruction. During forward extension of the plunger assembly, the carrier 50 is moved from behind to in front of a sample outlet port 98 at the sample collection point in the sampler body bore before the plunger assembly cap 48 is moved out of the bore. Then, with full extension of the plunger assembly, the carrier 50 is moved to a position close to the front of, but still within, the bore. In this manner, an open path is never established through the bore 34 between the interior of the vessel 26 and the outlet port 98, so that dry product is at all times prevented from freely moving from the vessel and through the bore to the outlet port.

After the plunger assembly 28 is extended into the vessel 26 to obtain a product sample, the handle 80 is manually moved leftward by the operator to reciprocate the plunger assembly rearward and retract it from the vessel. The handle and plunger assembly are retracted to the point where further retraction is prevented by engagement of the driver stop 84 with the rearward end 90 of the slot 86. At this point, the plunger assembly is fully retracted to its sample delivering position and its sample chamber 30 is positioned adjacent the outlet port 98 at the sample collection point in the sampler body bore 34. The product sample in the sample chamber then passes through the outlet port for collection in a container 100, which may conveniently be coupled to an outlet port adapter 102 by a quick connect/disconnect clamp 104. During rearward retraction of the plunger assembly, before the carrier 50 is moved over the outlet port 98, the cap 48 enters the sampler body bore. Again, dry product is prevented from freely moving from the vessel and through the bore to the outlet port, and only the product sample ever reaches the outlet port.

When the plunger assembly 28 is retracted to move the sample receiving opening 30 to the sample colleting point at the outlet port 98, a forward end 106 of the plunger assembly cap 48 is relatively far rearward from a forward opening 108 from the sampler body bore 34. An open forward section of the sampler bore, indicated generally at 110, then exists between the front of the plunger assembly and the forward bore opening, and is exposed through the opening to product in the vessel 26. Product from the vessel 26 can then enter and fill the front of the bore and, depending upon the nature of the product, can coalesce and block the bore in front of the plunger assembly if the sampling apparatus 20 remains idle for too long while the plunger assembly is in its retracted sample delivering position. Such a blockage could disable the sampler by blocking forward extension of the plunger assembly when a produt sample is next to be obtained.

To prevent product from entering and blocking the front of the sampler bore 34 when the plunger assembly 28 is fully retracted to its sample delivering position, the invention contemplates that the plunger assembly not remain in its sample delivering position during idle periods of the sampler assembly 20. Instead, the plunger assembly is moved forward to and locked against reciprocation at a parked position when the sampler assembly is to be idle, which parked position is intermediate the plunger assembly product sample delivering and receiving positions. Movement of the plunger assembly to the parked position places the front end 106 of the plunger assembly cap 48 close to and preferably at the bore forward opening 108, as indicated by the head of an arrow 112. The plunger assembly then closes the forward opening to the bore and prevents entry of product from the vessel into the bore while the sampler assembly is idle. Consequently, with the plunger assembly in the parked position, the sampler can remain idle for as long as desired without being rendered inoperative by the forward bore section 110 becoming blocked by product.

To move the plunger assembly 28 from the sample delivering to the parked position, the handle 80 is manually moved forward to extend the plunger assembly forward through the sampler body bore 34 until the indicator 94 is at the rearward end of the guide 60. At this point, the front 106 of the plunger assembly cap 48 is located close to and preferably at the bore forward opening 108 to close the opening, with the indicator 94 then visually informing the operator that the plunger assembly is in the parked position. Also at this point, the stop 84 carried by the driver 54 has been moved forward from the rearward end 90 of the guide slot 86 to a position in the slot adjacent to the circumferential slot extension 92. The plunger assembly can then be locked in the parked position by manual rotation of the handle 80, and therefore of the driver 54 and stop 84, clockwise (as viewed by the operator) to move the stop into the slot extension. When it is time to again operate the sampler assembly 20 to obtain a product sample, the handle is manually rotated counterclockwise to move the stop out of the slot extension to unlock the plunger assembly for reciprocation. The handle is then pushed forward to extend the plunger assembly into the vessel 26 to the sample receiving position. Further operation of the sampler assembly is then as above described.

While one embodiment of the invention has been described in detail, one skilled in the art thereof can devise various modifications and other embodiments without departing from the spirit and scope of the invention, as defined in the accompanying claims.

What is claimed is:

1. Sampling apparatus, comprising:
    a sampler operable to obtain discrete samples of product from a body of product, said sampler including a sampler body having a bore and a forward opening from said bore;
    plunger means having a product sample receiving opening;
    means for manually reciprocating said plunger means in said bore to each of a sample receiving position where said plunger means sample receiving opening is extended forward out of said forward bore opening, a sample delivering position where said plunger means sample receiving opening is retracted rearward to a position in said bore, and a parked position in said bore intermediate said sample receiving and delivering positions; and
    means for locking and unlocking said plunger means against and for reciprocation when said plunger means is in said parked position.

2. Sampling apparatus as in claim 1, wherein said plunger means has a forward end that is positioned rearward from said bore opening when said plunger means is in said sample delivering position and close to said bore opening when said plunger means is in said parked position.

3. Sampling apparatus as in claim 1, wherein said plunger means has a forward end that is positioned rearward from said bore opening when said plunger means is in said sample delivering position and at said bore opening when said plunger means is in said parked position.

4. Sampling apparatus as in claim 1, wherein said plunger means sample receiving opening comprises an annular opening in and circumferentially around said plunger means.

5. Sampling apparatus as in claim 1, wherein said means for locking and unlocking comprises means for locking and unlocking said means for reciprocating against and for reciprocation when said plunger means is in said parked position.

6. Sampling apparatus as in claim 1, wherein said means for manually reciprocating comprises a handle for being manually reciprocated by an operator, and means for connecting said handle and said plunger means for reciprocation of said plunger means by said handle.

7. Sampling apparatus as in claim 6, said means for connecting includes a driver rod connected at one end to said handle and at an opposite end to said plunger means, and including means for guiding and controlling reciprocation of said handle, said driver rod and said plunger means.

8. Sampling apparatus as in claim 7, wherein said means for guiding and controlling includes a guide sleeve around said driver rod, said guide sleeve having a longitudinal slot, and a stop carried by said driver rod and extending into said slot for reciprocation of said stop in said slot with reciprocation of said driver rod in said guide sleeve, said slot guiding said stop and driver rod during reciprocation of said driver rod and having forward and rearward ends that are engaged by said stop to limit the extent of longitudinal reciprocation of said stop and thereby said driver rod and plunger means.

9. Sampling apparatus as in claim 8, wherein said means for locking and unlocking said plunger means against and for reciprocation includes means for locking and unlocking said stop against and for reciprocation when said plunger means is in said parked position.

10. Sampling apparatus as in claim 8, wherein means for locking and unlocking said plunger means against and for reciprocation includes a circumferential extension of said slot into which said stop is moved when said plunger means is in said parked position to lock said stop and thereby said plunger means against reciprocation, and out of which extension said stop is moved to unlock said stop and thereby said plunger means for reciprocation.

11. Sampling apparatus as in claim 10, wherein said handle, drive rod, stop and plunger means can be rotated when said plunger means is in said parked position to move said stop into and out of said circumferential extension.

12. Sampling apparatus as in claim 1, including means for collecting product samples from said plunger means sample receiving opening when said plunger means is at said sample delivering position.

13. Sampling apparatus as in claim 12, wherein said means for collecting product samples includes an outlet from said sampler body bore at said plunger means sample delivering position.

14. Sampling apparatus as in claim 1, wherein said sampling apparatus is for obtaining discrete samples of dry product from a body of the dry product.

15. Sampling apparatus as in claim 1, wherein said plunger means sample receiving opening comprises a sample receiving recess in said plunger means.

16. Sampling apparatus as in claim 1, wherein said plunger means sample receiving opening comprises an annular recess in said plunger means.

17. A sampling apparatus for obtaining discrete samples of dry product from a body of dry product, comprising:
a sampler body having a bore extending therethrough and a forward opening from said bore;
a sampling plunger having a product sample receiving recess intermediate forward and rearward ends thereof;
means for manually reciprocating said plunger in said bore in a forward direction to extend said forward end of said plunger and said sample receiving recess through said bore forward opening to a sample receiving position in the body of dry product to receive a product sample in said recess, for then reciprocating said plunger in a rearward direction to retract said plunger sample receiving recess and forward end through said bore opening to a sample delivering position in said bore, and for then reciprocating said plunger to a parked position in said bore forward from said sample delivering position and rearward from said sample receiving position, and
means for locking and unlocking said plunger against and for reciprocation when said plunger is in said parked position.

18. Sampling apparatus as in claim 17, wherein said plunger forward end is positioned rearward from said bore forward opening when said plunger is in said sample delivering position and close to said bore forward opening when said plunger is in said parked position.

19. Sampling apparatus as in claim 17, wherein said plunger forward end is positioned rearward from said bore forward opening when said plunger is in said sample delivering position and at said bore opening when said plunger is in said parked position.

20. Sampling apparatus as in claim 17, wherein said plunger product sample receiving recess comprises an annular recess in and circumferentially around said plunger.

21. Sampling apparatus as in claim 17, wherein said means for locking and unlocking said plunger against and for reciprocation comprises means for locking and unlocking said manually reciprocating means against and for reciprocation when said plunger is in said parked position.

22. Sampling apparatus as in claim 21, wherein said means for manually reciprocating comprises a handle for being manually moved by an operator, a driver rod connected at one end to said handle and at an opposite end to said plunger, and means for guiding and controlling reciprocation of said handle, said driver rod and said plunger.

23. Sampling apparatus as in claim 22, wherein said means for guiding and controlling includes a guide sleeve around said driver rod, said guide sleeve having a longitudinal slot, and a stop carried by said driver rod and extending into said slot for reciprocation in said slot with reciprocation of said driver rod in said guide sleeve, said slot guiding said stop and driver rod during reciprocation of said driver rod and said slot having forward and rearward ends that are engaged by said stop to limit the longitudinal extent of reciprocation of said stop, said driver rod and said plunger, and said means for locking and unlocking said plunger means against and for reciprocation including means for locking and unlocking said stop against and for reciprocation in said slot when said plunger is at said parked position.

24. Sampling apparatus as claim 23, wherein means for locking and unlocking includes a circumferential extension of said slot into which said stop is moved when said plunger is in said parked position to lock said plunger against reciprocation and out of which said stop is moved to unlock said plunger for reciprocation, and wherein said handle, drive rod, stop and plunger can be rotated when said plunger is in said parked position to move said stop into and out of said circumferential extension.

25. A method of sampling a dry product, comprising the steps of:
providing a sampler body having a longitudinal bore and a forward opening from the bore;
positioning a plunger, having a sample receiving opening intermediate forward and rearward ends thereof, in the bore;
manually extending the plunger forward through the bore to a sample receiving position where the plunger forward end and sample receiving opening are projected out of the bore forward opening and into a body of dry product to receive in the sample receiving opening a sample of dry product;
after said extending step, manually retracting the plunger rearward through the bore to a sample delivering position to deliver the product sample in the plunger sample receiving opening to a sample collecting point in the bore, the forward end of the plunger at the sample delivering position being rearward from the bore forward opening, so that a length of the bore then exists between the plunger forward end and the bore forward opening;
removing the dry product sample from the sample receiving opening at the sample delivering position;
after said removing step, manually moving the plunger forward to a parked position intermediate the sample delivering and the sample receiving positions; and
manually locking the plunger in the parked position.

26. A method as in claim 25, wherein said step of manually moving the plunger forward to the parked position comprises manually moving the plunger forward to position the plunger forward end close to the bore opening, so that the plunger doses the bore rearward from the plunger forward end.

27. A method as in claim 25, wherein said step of manually moving the plunger forward to the parked position comprises manually moving the plunger forward to position its forward end at the bore opening, so that the plunger doses the bore rearward from the bore forward opening.

* * * * *

UNITED STATES PATENT AND TRADEMARK OFFICE
CERTIFICATE OF CORRECTION

PATENT NO.    : 6,807,873 B2
DATED         : October 26, 2004
INVENTOR(S)   : Ben E. Jaeger It is certified that error appears in the above-identified patent and that said Letters Patent is hereby corrected as shown below:

Column 8,
Line 43, before "said" insert -- wherein --

Column 10,
Lines 59 and 64, "doses" should be -- closes --

Signed and Sealed this

Seventeenth Day of May, 2005

JON W. DUDAS
*Director of the United States Patent and Trademark Office*